United States Patent
Kokeguchi

(10) Patent No.: US 9,504,633 B2
(45) Date of Patent: Nov. 29, 2016

(54) WATER-IN-OIL TYPE EMULSIFIED COSMETIC

(75) Inventor: Yuki Kokeguchi, Narita (JP)

(73) Assignee: KOKYU ALCOHOL KOGYO CO., LTD., Chiba (JP)

( * ) Notice: Subject to any disclaimer, the term of this patent is extended or adjusted under 35 U.S.C. 154(b) by 630 days.

(21) Appl. No.: 12/647,155

(22) Filed: Dec. 24, 2009

(65) Prior Publication Data

US 2010/0166684 A1  Jul. 1, 2010

Related U.S. Application Data

(60) Provisional application No. 61/204,712, filed on Jan. 9, 2009.

(30) Foreign Application Priority Data

Dec. 25, 2008  (JP) .................................. 2008-330043

(51) Int. Cl.

| A61K 8/06 | (2006.01) |
|---|---|
| A61K 8/30 | (2006.01) |
| A61Q 1/00 | (2006.01) |
| A61K 8/19 | (2006.01) |
| A61K 8/25 | (2006.01) |
| A61K 8/31 | (2006.01) |
| A61K 8/37 | (2006.01) |
| A61K 8/60 | (2006.01) |
| A61K 8/81 | (2006.01) |
| A61Q 1/02 | (2006.01) |
| A61Q 17/04 | (2006.01) |

(52) U.S. Cl.
CPC . *A61K 8/06* (2013.01); *A61K 8/19* (2013.01); *A61K 8/25* (2013.01); *A61K 8/31* (2013.01); *A61K 8/37* (2013.01); *A61K 8/60* (2013.01); *A61K 8/8182* (2013.01); *A61Q 1/00* (2013.01); *A61Q 1/02* (2013.01); *A61Q 17/04* (2013.01)

(58) Field of Classification Search
None
See application file for complete search history.

(56) References Cited

U.S. PATENT DOCUMENTS

| 5,516,506 A * | 5/1996 | Fogel .............................. 424/59 |
| 2004/0197361 A1* | 10/2004 | Oguchi et al. ................. 424/401 |
| 2005/0118210 A1* | 6/2005 | Kachi et al. .................. 424/401 |
| 2007/0093619 A1* | 4/2007 | Bui et al. ...................... 525/477 |
| 2007/0110702 A1* | 5/2007 | Ehara .......................... 424/70.31 |
| 2007/0264207 A1 | 11/2007 | Tsuchikawa et al. |
| 2007/0269470 A1* | 11/2007 | Takeda et al. ................. 424/401 |
| 2008/0260663 A1* | 10/2008 | Yamato .................... A61K 8/85 424/59 |

FOREIGN PATENT DOCUMENTS

| JP | 3-095107 | 4/1991 |
| JP | 10-175819 | 6/1998 |
| JP | 2001-058922 | 3/2001 |
| JP | 2005-112823 | 4/2005 |
| JP | 2008-100940 | 5/2008 |
| JP | 2008-127306 | 6/2008 |
| JP | 220-162965 | 7/2008 |
| JP | 2008-162965 | 7/2008 |

* cited by examiner

*Primary Examiner* — Robert A Wax
*Assistant Examiner* — Randeep Singh
(74) *Attorney, Agent, or Firm* — Norris McLaughlin & Marcus, P.A.

(57) ABSTRACT

There is provided a novel water-in-oil type emulsified cosmetic comprising a diester of neopentylglycol with isononanoic acid. Said cosmetic exhibits not only the refreshed feeling on use without unfavorable stickiness after application, but also proper oily feeling. There are obtained good affinity to the skin, little occurrence of creasing and/or make-up deterioration, no oily sheen upon the elapse of long periods of time after application, and little irritation to the skin and excellent safety to the skin. In addition, the present cosmetic is able to be removed with commercially available cleansing agents. Moreover, the dispersibility of pigments as well as the storage stability is excellent.

A water-in-oil type emulsified cosmetic comprising (A) 10 to 60 parts by mass of a diester represented by the following formula (I):

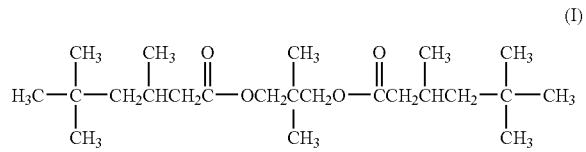

(B) 1.0 to 11 parts by mass of a nonionic surfactant, (C) 0.3 to 11 parts by mass of an oil-soluble and/or water-soluble thickener, (D) 0.1 to 30 parts by mass of fine particles, and (E) 5.0 to 75 parts by mass of water, wherein the total of (A), (B), (C), (D) and (E) is 100 parts by mass.

15 Claims, No Drawings

WATER-IN-OIL TYPE EMULSIFIED COSMETIC

REFERENCE TO RELATED APPLICATION

This application claims the benefit of the filing date of Provisional Application No. 61/204,712 filed Jan. 9, 2009.

BACKGROUND OF THE INVENTION

The present invention relates to a water-in-oil type emulsified cosmetic, more specifically to a water-in-oil type emulsified cosmetic used for make-up cosmetics, sun-care cosmetics, etc.

In the prior art, silicone has been mainly used in water-in-oil type emulsified cosmetics such as make-up cosmetics and sun-care cosmetics. For instance, there is known a water-in-oil type emulsified cosmetic comprising (A) an oily component containing silicone oil, (B) a copolymer obtained by polymerizing an organosiloxane monomer having a predetermined structure with a radical polymerizable monomer containing a predetermined N-atom, (C) fine particles, and (D) water in predetermined amounts in Japanese Patent Application Laid-Open 2008-100,940. The invention disclosed in this patent application provides the water-in-oil type emulsified cosmetic which controls attaching property of the fine particles to crista cutis and sulcus cutis, so that the cosmetic has high attachability of fine particles to the skin to attain an even, natural and beautiful finish, and which has good cosmetic-holding ability and excellent emulsion stability.

There is also known a water-in-oil type emulsified cosmetic comprising dimethylpolysiloxane, a condensate of a glycerin aliphatic acid ester with a dicarboxylic acid, a predetermined oil component, fine particles and water in Japanese Patent Application Laid-Open 1998-175, 819. In this patent application, as the oil component, mention is made of various esters such as isocetyl adipate, isodecyl isononanoate, isotridecyl isononanoate, isononyl isononanoate, neopentylglycol di-2-ethylhexanoate, neopentylglycol dicaprate, etc. The invention disclosed in this patent application provides the water-in-oil type emulsified cosmetic which exhibits good feeling on use, good emulsion stability and good cosmetic-holding ability, as well as excellent refreshing feeling upon application on the skin, and which is excellent in dispensability of fine particles, so that the cosmetic exhibits a good UV-protective effect when UV-protective fine particles such as microparticles of titanium oxide, zinc oxide and iron oxide are blended in the cosmetic.

In addition, there is also known a water-in-oil type emulsified cosmetic comprising one or more of cyclic silicone tetramer, pentamer and hexamer; sorbitan monostearate and/or diglyceryl monoisostearate; an oily component other than the above cyclic silicone; and water in predetermined amounts in Japanese Patent Application Laid-Open 1991-95,107. This patent application describes that use may be made of various substances such as, for instance, hydrocarbons, fats and oils, waxes, higher alcohols, higher fatty acids, esters, etc, as the oily component. The invention disclosed in this patent application provides the water-in-oil type emulsified cosmetic wherein the stickiness and the oiliness are improved, the spreading is easy and the stability with the elapse of time is very excellent in spite of containing plenty of cyclic silicones.

However, in the water-in-oil type emulsified cosmetic in which silicone is mainly used, unfavorable oiliness after application has not yet sufficiently been improved. In addition, said water-in-oil type emulsified cosmetic has a difficulty of the affinity with the skin. Moreover, pigments contained in the cosmetic are accumulated at wrinkles and sulcus cutises, so that the finish color becomes uneven, i.e. so called creasing easily occurs, and a make-up deterioration also easily occurs. In addition, characteristic oily sheen easily occurs upon the elapse of long periods of time after application. And, there is a problem that the cosmetic is difficult to be removed with commercially available cleansing agents.

In order to reduce unfavorable feeling such as oiliness and stickiness, and to obtain a water-in-oil type emulsified cosmetic which has smooth feeling, and is excellent in safety, and is excellent in, flow ability, oil-soluble gelatinizing agents were contained in the cosmetic by way of trial. For instance, there is known a water-in-oil type emulsified cosmetic comprising (a) dextrin esterified with an aliphatic acid including a blanched aliphatic acid and/or unsaturated aliphatic acid, or (b) dextrin esterified with a straight chain aliphatic acid, as a gelatinizing agent in Japanese Patent Application Laid-Open 2001-58,922. In the invention disclosed in this patent application, the cosmetic may comprise, in addition to the aforesaid ingredients, an oil agent such as hydrocarbons, fats and oils, waxes, esters, aliphatic acids, higher alcohols, silicone oils, fluor-type oils, and lipophilic surfactants. In the Examples, use is made of neopentylglycol di-2-ethylhexanoate, propyleneglycol dicaprate, etc. as the oil agent.

In Japanese Patent Application Laid-Open 2008-127,306, there is also proposed a water-in-oil type emulsified cosmetic comprising (A) a silicone type surfactant, (B) an oil agent, (C) a gelatinizing agent for oils, (D) a water-soluble polymer thickener and (E) water. The invention disclosed in this patent application provides a water-in-oil type emulsified cosmetic wherein good stability with the elapse of time, high moisturizing effect and excellent feeling on use without stickiness are attained by adding the silicone surfactant. As the oil agent, use is made of hydrocarbon oils, higher alcohols, higher aliphatic acids, olive oils, jojoba oils, ester oils such as neopentylglycol dicaprate, silicone oils, etc. In the Examples, squalane and a liquid paraffin which are included in hydrocarbon oils, and dimethicone which is included in silicone oils are used.

However, in the aforementioned water-in-oil type emulsified cosmetics, unfavorable feeling such as oiliness and stickiness has not yet sufficiently reduced, and the storage stability was not sufficient.

Meanwhile, there is known a diester, which is represented by the following formula (I), obtained by reacting isononanoic acid with neopentylglycol in Japanese Patent Application Laid-Open 2008-162,965. Said diester is used as a cleansing cosmetic. In said cleansing cosmetic, the wash-out effect of make-up cosmetics is considerably excellent. In this patent application, there is no description that said diester may be used as an oil agent in water-in-oil type emulsified cosmetics such as make-up cosmetics. Moreover, it is not known that said diester has been used as an oil agent in water-in-oil type emulsified cosmetics.

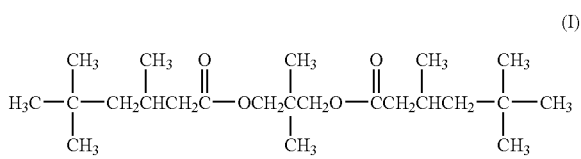

SUMMARY OF THE INVENTION

The present invention provides a novel water-in-oil type emulsified cosmetic comprising a diester obtained by reacting isononanoic acid with neopentylglycol as an oily component. In order to overcome various drawbacks of the prior art water-in-oil type emulsified cosmetics, the present inventors have conducted investigations. As a result, we have found that there was obtained a water-in-oil type emulsified cosmetic which exhibits the excellent effects, which have not been attained in the prior art water-in-oil type emulsified cosmetics, by using a diester obtained by reacting isononanoic acid with neopentylglycol, in combination with the predetermined components, i.e. a nonionic surfactant, an oil-soluble and/or water-soluble thickener, fine particles and water, in the predetermined amounts, which leads to the present invention.

That is, the present invention is (1) a water-in-oil type emulsified cosmetic comprising (A) 10 to 60 parts by mass of a diester represented by the following formula (I):

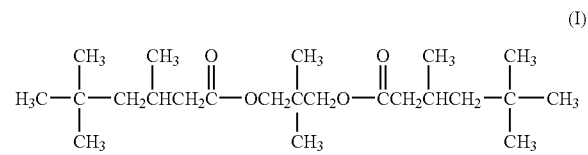

(B) 1.0 to 11 parts by mass of a nonionic surfactant, (C) 0.3 to 11 parts by mass of an oil-soluble and/or water-soluble thickener, (D) 0.1 to 30 parts by mass of fine particles, and (E) 5.0 to 75 parts by mass of water, wherein the total of (A), (B), (C), (D) and (E) is 100 parts by mass.

As preferred embodiments of the present invention, mention may be made of:

(2) the water-in-oil type emulsified cosmetic according to the above (1), wherein the amount of the diester represented by the formula (I) is 12 to 55 parts by mass, (3) the water-in-oil type emulsified cosmetic according to the above (1), wherein the amount of the diester represented by the formula (I) is 14 to 50 parts by mass, (4) the water-in-oil type emulsified cosmetic according to any one of the above embodiments (1) to (3), wherein the amount of the nonionic surfactant (B) is 1.1 to 9.8 parts by mass, (5) the water-in-oil type emulsified cosmetic according to any one of the above embodiments (1) to (3), wherein the amount of the nonionic surfactant (B) is 1.2 to 9.6 parts by mass, (6) the water-in-oil type emulsified cosmetic according to any one of the above embodiments (1) to (5), wherein the amount of the oil-soluble and/or water-soluble thickener (C) is 0.4 to 9.8 parts by mass, (7) the water-in-oil type emulsified cosmetic according to any one of the above embodiments (1) to (5), wherein the amount of the oil-soluble and/or water-soluble thickener (C) is 0.5 to 9.6 parts by mass, (8) the water-in-oil type emulsified cosmetic according to any one of the above embodiments (1) to (7), wherein the amount of the fine particles (D) is 0.2 to 28 parts by mass, (9) the water-in-oil type emulsified cosmetic according to any one of the above embodiments (1) to (7), wherein the amount of the fine particles (D) is 0.3 to 26 parts by mass,

(10) the water-in-oil type emulsified cosmetic according to any one of the above embodiments (1) to (9), wherein the amount of water (E) is 10 to 68 parts by mass,

(11) the water-in-oil type emulsified cosmetic according to any one of the above embodiments (1) to (9), wherein the amount of water (E) is 15 to 66 parts by mass,

(12) the water-in-oil type emulsified cosmetic according to any one of the above embodiments (1) to (11), wherein the nonionic surfactant (B) is at least one selected from the group consisting of sorbitan monoisostearate, lipophilic glycerin monostearate, glyceryl stearate (SE), sorbitan sesquiisostearate, polyglyceryl-2 isostearate, polyglyceryl-2 diisostearate, polyglyceryl-2 triisostearate and sorbitan oleate,

(13) the water-in-oil type emulsified cosmetic according to any one of the above embodiments (1) to (11), wherein the nonionic surfactant (B) is at least one selected from the group consisting of sorbitan monoisostearate, lipophilic glycerin monostearate, sorbitan sesquiisostearate, polyglyceryl-2 isostearate and sorbitan oleate,

(14) the water-in-oil type emulsified cosmetic according to any one of the above embodiments (1) to (13) for make-up and sun-care cosmetics.

The water-in-oil type emulsified cosmetic of the present invention exhibits not only the refreshed feeling on use without unfavorable stickiness after application, but also the proper oily feeling because the cosmetic contains an diester obtained by reacting isononanoic acid with neopentylglycol as an oily component. There are obtained good affinity to the skin, little occurrence of creasing and/or make-up deterioration, no oily sheen upon the elapse of long periods of time after application, and little irritation to the skin and excellent safety to the skin. In addition, the present cosmetic is able to be removed with commercially available cleansing agents. Moreover, the dispersibility of pigments as well as the storage stability is excellent.

DETAILED DESCRIPTION OF THE INVENTION

Component (A) in the present invention is the diester represented by the following formula (I). Said diester is described in detail in the aforesaid patent application (Japanese Patent Application Laid-Open 2008-162,965).

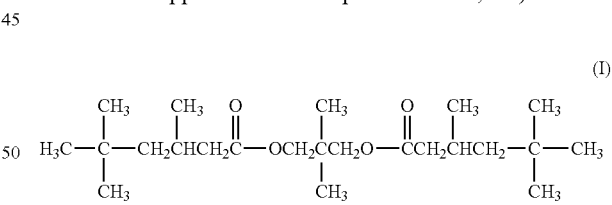

This diester may be prepared using known preparation processes of diesters. For example, 2 moles of isononanoic acid and one mole of neopentylglycol are placed in a reactor and then, the reaction is carried out, preferably while nitrogen bubbling at atmospheric pressure, preferably under reflux while heating at 200 to 220 degrees C. until no produced water is distilled off any more, preferably for 10 to 50 hours. In the above reaction, it is preferred to use a solvent and a catalyst. As the solvent, for example, benzene and toluene may be mentioned. As the catalyst, mention may be made of, for example, sodium hydroxide, paratoluene sulphonic acid, sulfuric acid and hydrochloric acid, etc. After the reaction is completed, the catalyst is removed by washing the content in the reactor with water. The reaction products obtained after washing with water is heated under reduced pressure, for example, at 10 mmHg, for example at 120 degrees C. for 30 minutes, to distill the solvent off, and then dried. Next, the product thus obtained is purified by distillation, for example, while nitrogen bubbling under reduce pressure of 3 mmHg.

The upper limit of the amount of Component (A) mentioned above is 60 parts by mass, preferably 55 parts by mass, and more preferably 50 parts by mass, based on 100 parts by mass of the total amount of Components (A), (B), (C), (D) and (E), and the lower limit is 10 parts by mass, preferably 12 parts by mass, more preferably 14 parts by mass, based on 100 parts by mass of the total amount of Components (A), (B), (C), (D) and (E). If the amount exceeds the above upper limit, the cosmetic is poor in feeling on use, cosmetic-holding ability and storage stability. If the amount is below the above lower limit, the dispersibility of the pigments is poor.

It is preferred that the nonionic surfactant of Component (B) used in the present invention is one which may successfully emulsify Component (A) mentioned above. For example, use is made of sorbitan aliphatic acid esters, glycerin aliphatic acid esters, polyglycerin aliphatic acid esters, propyleneglycol aliphatic acid esters, polyethyleneglycol aliphatic acid esters, sucrose aliphatic acid esters, polyoxyethylenealkylethers, polyoxyethylenesorbitan aliphatic acid esters, polyoxyethylenesorbitol aliphatic acid esters, polyoxyethyleneglycerin aliphatic acid esters, polyoxyethylenepropyleneglycol aliphatic acid esters, polyoxyethylene castor oils, polyoxyethylene hydrogenated castor oils, polyoxyethylene phytosterol ethers, polyoxyethylene cholestanol ethers, polyoxyethylene cholesteryl ethers, etc. Among these, use are preferably made of sorbitan aliphatic acid esters, glycerin aliphatic acid esters, polyglycerin aliphatic acid esters. More preferably, use is made of sorbitan monoisostearate, lipophilic glycerin monostearate, glyceryl stearate (SE), sorbitan sesquiisostearate, polyglyceryl-2 isostearate, polyglyceryl-2 diisostearate, polyglyceryl-2 triisostearate, sorbitan oleate. The nonionic surfactant of Component (B) may be used each alone, or in combination of two or more of these.

The upper limit of the amount of the nonionic surfactant of Component (B) is 11 parts by mass, preferably 9.8 parts by mass, more preferably 9.6 parts by mass, based on 100 parts by mass of the total amount of Components (A), (B), (C), (D) and (E), and the lower limit is 1.0 part by mass, preferably 1.1 parts by mass, more preferably 1.2 parts by mass, based on 100 parts by mass of the total amount of Components (A), (B), (C), (D) and (E). If the amount exceeds the above upper limit, the appearance of the water-in-oil type emulsified cosmetic deteriorates and, in addition, the stability decreases, so that the cosmetic may not be prepared. If the amount is below the above lower limit, similarly, the stability decreases, so that the cosmetic may not be prepared.

The oil-soluble and/or water-soluble thickener of Component (C) is known. One which is usually blended in cosmetics may be used without any limitation. As the oil-soluble thickener, use is made of, for example, inurin derivatives such as inurin stearate; dextrin derivatives such as dextrin palmitate and dextrin (palmitate/ethylhexanoate); glyceryl(behenate/eicosane dioate); polyamide resins such as ester-terminated polyamide resins and amide-terminated polyamide resins; amino acid derivatives such as dibutyllauroylglutamide and dibutylethylhexanoylglutamide; waxes such as beeswax, candelilla wax, carnauba wax, ozokerite, ceresin, polyethylene, microcrystalline wax and synthetic wax; di(C20-40)alkyl dimer-dilinoleate; (ethylene/propylene) copolymers, etc. Preferably use is made of dextrin palmitate, glyceryl(behenate/eicosane dioate), ester-terminated polyamide resins, amide-terminated polyamide resins, dibutyllauroylglutamide, dibutylethylhexanoylglutamide and di(C20-40)alkyl dimer-dilinoleate.

As the water-soluble thickener, use is made of for example, natural types such as xanthan gum, gellan gum, guar gum, gum arabic, sodium alginate, carrageenan, and cellulose; semi-synthetic types such as methylcellulose, hydroxyethylcellulose, hydroxypropylcellulose, hydroxypropylmethylcellulose, and carboxymethylcellulose; and synthetic types such as carboxyvinylpolymer (carbomer), sodium polyacrylate, and (acryloyldimethyltaurin ammonium/VP) copolymer.

The oil-soluble and/or water-soluble thickener of Component (C) may be used each alone, or in combination of two or more of these.

The upper limit of the amount of the oil-soluble and/or water-soluble thickener of Component (C) is 11 parts by mass, preferably 9.8 parts by mass, more preferably 9.6 parts by mass, based on 100 parts by mass of the total amount of Components (A), (B), (C), (D) and (E), and the lower limit is 0.3 part by mass, preferably 0.4 part by mass, more preferably 0.5 part by mass, based on 100 parts by mass of the total amount of Components (A), (B), (C), (D) and (E). If the amount exceeds the above upper limit, the water-in-oil type emulsified cosmetic itself hardens, so that the feeling by touch deteriorates, and the stability is poor. If the amount is below the above lower limit, the stability decreases, so that the cosmetic may not be prepared.

The fine particles of Component (D) are also known. Ones which are usually blended in cosmetics may be used without any limitation. Both organic and inorganic fine particles may be used. For the inorganic fine particles, use may be made of, for example, titanium oxide, iron oxide such as iron oxide yellow, iron oxide red (Bengara) and iron oxide black, zirconium oxide, zinc oxide, cerium oxide, magnesium oxide, barium sulfate, calcium sulfate, magnesium sulfate, calcium carbonate, magnesium carbonate, talc, mica, kaolin, sericite, moscovite, synthetic mica, beni-unmo (lepidolite), phologopite, biotite, lepidolite, silicic acid, silicic anhydride, aluminum silicate, magnesium silicate, aluminum magnesium silicate, calcium silicate, barium silicate, strontium silicate, metal tungstate, vermiculite, hydroxyapatite, higilite, zeolite, bentonite, montmorilonite, hectorite, ceramic powder, calcium hydrogen-phosphate, alumina, aluminum hydroxide and boron nitride.

For the organic fine particles, use may be made of, for example, polyamide powder, polyester powder, polyethylene powder, polypropylene powder, polystyrene powder, polyurethane, benzoguanamine powder, polymethyl benzoguanamine powder, polymethyl methacrylate powder, tetrafluoroethylene powder, silk powder, nylon powder, nylon-12, nylon-6, (dimethicone/vinyldimethicone) crosspolymer (crosslinked type silicone powder), styrene-acrylic acid copolymer, divinylbenzene-styrene copolymer, vinyl resin, phenol resin, urea resin, fluoroplastic, silicone resin, acrylic resin, epoxy resin, melamine resin, polycarbonate resin, microcrystalline fibre powder, rice starch and lauroyl lysine.

Preferably pigments may also be used as the fine particles. Mention may be made of, for example, inorganic red pigments such as iron oxide, iron hydroxide and iron titanate; inorganic brown pigments such as gamma-iron oxide; inorganic yellow pigments such as iron oxide yellow and ocher; inorganic black pigments such as iron oxide black and carbon black; inorganic violet pigments such as manganese violet and cobalt violet; inorganic green pigments such as chromium hydroxide, chromium oxide, cobalt oxide and cobalt titanate; inorganic blue pigments such as Prussian blue and ultramarine; tar-type colorants; tar-type colorants modified with lake; natural colorants; natural colorants modified with lake; and composite particles composed of these fine particles, which are colored pigments. Mention may also be made of, for example, pearlescent pigments such as mica coated with titanium oxide, bismuth oxychloride, bismuth oxychloride coated with titanium oxide, talc coated with titanium oxide, fish scales flakes (natural pearl essence originated from fish) and colored mica coated with titanium oxide ($TiO_2$ coated mica); metal powder pigments (pearlescent pigments) such as aluminum powder, copper powder, stainless steel powder; and lame agents such as (PET/polymethylmethacrylate) laminate.

Among these, it is preferred to use titanium oxide, talc, iron oxide such as iron oxide yellow, iron oxide black and iron oxide red (Bengara), zinc oxide, ultramarine and $TiO_2$ coated mica, which are preferably hydrophobicated. The fine particles of Component (D) may be used each alone, or in combination of two or more of these.

The upper limit of the amount of the fine particles of Component (D) is 30 parts by mass, preferably 28 parts by mass, more preferably 26 parts by mass, based on 100 parts by mass of the total amount of Components (A), (B), (C), (D) and (E), and the lower limit is 0.1 part by mass, preferably 0.2 part by mass, more preferably 0.3 parts by mass, based on 100 parts by mass of the total amount of Components (A), (B), (C), (D) and (E). If the amount exceeds the above upper limit, the feeling on use deteriorates when the water-in-oil type emulsified cosmetic is applied. If the amount is below the above lower limit, the fine particles may not sufficiently exhibit the intrinsic effect such as stable chromatic effect.

As water of Component (E), use is made of, for example, pure water and demineralized water. Inclusion of water may reduce stickiness and give refresh feeling when the water-in-oil type emulsified cosmetic is applied, so that the applicability may advance. The upper limit of the amount of water of Component (E) is 75 parts by mass, preferably 68 parts by mass, more preferably 66, parts by mass, based on 100 parts by mass of the total amount of Components (A), (B), (C), (D) and (E), and the lower limit is 5.0 parts by mass, preferably 10 parts by mass, more preferably 15 parts by mass, based on 100 parts by mass of the total amount of Components (A), (B), (C), (D) and (E). If the amount exceeds the above upper limit, the stability of the water-in-oil type emulsified cosmetic is poor. If the amount is below the above lower limit, stickiness may occur in the water-in-oil type emulsified cosmetic and refresh feeling and good applicability may not be obtained when the water-in-oil type emulsified cosmetic is applied.

In the water-in-oil type emulsified cosmetic of the present invention, the following substances may be used as an oil agent in an amount that they does not spoil the effects of the present invention. For example, mention may be made of hydrocarbon oils such as liquid paraffin, squalane and polyisobutene; higher alcohols such as oleyl alcohol, milistyl alcohol, cetanol, stearyl alcohol, isostearyl alcohol, cetearyl alcohol, octyldodecanol, aralkylalcohol, hydrogenated rapeseed oil alcohol, behenyl alcohol and decyltetradecanol; higher aliphatic acids such as palmitic acid, myristic acid, stearic acid and isostearic acid; ester oils such as olive oil, jojoba seed oil, ethylhexyl isononanoate, isononyl isononanoate, isotridecyl isononanoate, neopentylglycol dicaprate, glyceryl tri(caprylate/caprate), cetyl ethylhexanoate, hexyldecyl ethylhexanoate, neopentylglycol diethylhexanoate, trimethylolpropane triethylhexanoate, triethylhexanoin, pentaerythrityl tetraethylhexanoate, hexyl laurate, diisobutyl adipate, diethylhexyl succinate, bisethoxydiglycol succinate, ethylhexyl palmitate, cetyl palmitate, isopropyl isostearate, hexyldecyl isostearate, isostearyl isostearate, triisostearin, trimethylolpropane triisostearate, pentaerythrityl tetraisostearate, hydrogenated castor oil isostearate, isopropyl myristate, octyldodecyl myristate, oleyl oleate, oleyl erucate, octyldodecyl erucate, ethylhexyl hydroxystearate, octyldodecyl stearoyloxystearate, isostearyl neopentanoate, octyldodecyl neopentanoate, octyldodecyl neodecanoate, diisostearyl malate, polyglyceryl-2 tetraisostearate, dimer dilinoleyl dimer dilinoleate, hydrogenated castor oil dimer dilinoleate, (polyglyceryl-2 isostearate/dimer dilinoleic acid)copolymer, dipentaerythrityl hexa(hydroxystearate/stearate/rosinate) and (diglycerin/dilinoleic acid/hydroxystearic acid) copolymer; silicone oils such as cyclomethicone, phenyltrimethicone and dimethicone. Preferably use is made of squalane, octyldodecyl neopentanoate, hexyldecyl isostearate, diisostearyl malate, (diglycerin/dilinoleic acid/hydroxystearic acid) copolymer and (polyglyceryl-2 isostearate/dimer dilinoleic acid) copolymer.

The water-in-oil type emulsified cosmetic of the present invention may further contain, in addition to the aforesaid components, conventional additives, for example, multivalent alcohols such as 1,2-pentanediol, 1,2-hexanediol, 1,3-butylene glycol, propylene glycol, dipropylene glycol, glycerin; alcohols such as ethanol; vegetable oils such as lavender oil; animal oils such as lanolin; paste oils such as sodium isostearoylbutyrate; semi-solid oils such as vaseline; solid fats such as shea butter and hydrogenated palm kernel oil; agents for improving the feeling by touch such as spheric nylon powder and crosslinked type silicone powder; extracts; medicinal agents; cosmetic ingredients; microbicides; antibacterial agents; anti-inflammatories; preservatives; antioxidants; UV absorbers; UV scattering agents; moisturizing agents; chelating agents; pH adjusting agents; perfumes; colorants; and vitamins, which are all usually blended in water-in-oil type emulsified cosmetics, in an amount that they does not spoil the effects of the present invention. The water-in-oil type emulsified cosmetic of the present invention may further contain a silicone type surfactant such as dimethicone copolyol, in addition to the aforesaid nonionic surfactant of Component (B), in an amount that it does not spoil the effects of the present invention. The silicone type surfactant may be blended in the cosmetic in an amount of at most about 10 parts by mass, based on 100 parts by mass of Component (A), although the amount is not necessarily limited to these, because it depends on kinds and amounts of other components.

The water-in-oil type emulsified cosmetic of the present invention may be prepared using known processes. For example, Components (A), (B) and (C), and optional components other than those which are water-soluble or are in a form of fine particles, are dissolved homogenously at 100 degrees C. to obtain a mixture, to which Component (D) and the optional components in a form of fine particles are added to make a dispersion. Then, to the dispersion thus obtained are added Component (E) and the optional components which are water-soluble to make an emulsion-dispersion. Next, the emulsion-dispersion is cooled to room temperature while stirring. In this way, the water-in-oil type emulsified cosmetic of the present invention may easily be prepared.

In the following Examples, the present invention will be described in more detail, but not limited thereto.

EXAMPLES

Each component used in the Examples and Comparative Examples was as follows;

Component (A): the Compound Represented by the Formula (I), which May be Called "Neopentylglycol Diisononanoate".

Use was made of one which was prepared as follows:

Synthesis of Neopentylglycol Diisononanoate

In a four-neck 2,000 mL glass flask equipped with a stirrer, a thermometer, a nitrogen gas inlet tube, and a Dean-Stark condenser with a water measuring trap were placed 208.2 g (2.0 mol) of neopentylglycol, 632.4 g (4.0 mol) of isononanoic acid, 100 mL of toluene as a solvent and 0.8 g of paratoluenesulfonic acid as a catalyst. Then, the reaction mixture was heated to 200 degrees C. under a flow of nitrogen gas in a rate of 10 mL/min. at atmospheric pressure. The reaction was carried out under reflux with heating at that temperature for 10 hours while distilling off the produced water with the solvent azeotropically. When the distillation-off water subsided, the temperature was raised to 220 degrees C. to further continue the reaction. When the distillation-off water stopped, the reaction was terminated. It took about 20 hours from the start of the reaction to this point. The reaction product thus obtained was transferred to a 3,000 mL separating funnel. The catalyst used was removed by washing with 200 mL of water twice. Then, the oily phase was transferred to a four-neck 2,000 mL glass flask equipped with a stirrer, a thermometer, a nitrogen gas inlet tube, and a Dean-Stark condenser with a water measuring trap. Toluene as the solvent and water were distilled off by heating at 120 degrees C. under reduced pressure of about 10 mmHg for 30 minutes and then the product was dried. 730 g of the intended substance was obtained. The yield was about 95%. 730 g of the reaction product thus obtained was placed in a 2,000 mL glass Claisen flask and distilled under reduced pressure of 3 mmHg under bubbling of nitrogen in a rate of 1 mL/min. 620 g of the intended substance was obtained by recovering the distillate at 160 to 170 degrees C. The yield was 85%.

The product thus obtained was analyzed by infrared absorption spectroscopy (apparatus: Spectrum One from Perkin-Elmer, with ATR method) and by gas chromatography (apparatus: Agilent 6850 from Agilent; column: DB-1 from Agilent with an inner diameter of 0.25 mm, a length of 15 m and a film thickness of 0.1 μm; injection method: split method, 50:1; column temperature: elevating the temperature from 100 to 250 degrees C. in a rate of 5 degrees C./min. and maintaining at 250 degrees C. for 5 minutes; injection temperature: 250 degrees C.; carrier gas: He; detecting method: FID 230 degrees C.; injection volume: 1.0 microliter). As a result, according to the infrared absorption spectroscopy, there were detected absorbances at about 2,960 to 2,870 $cm^{-1}$, about 1,735 $cm^{-1}$, about 1,475 $cm^{-1}$, and about 1,150 $cm^{-1}$, which are due to methyl groups, methylene groups (C—H stretching), ester groups (C=O stretching), methylene groups (C—H bending) and ester groups (C—O stretching), respectively. The result of the gas chromatography indicated that the product had a purity of 95% or more. These analyses demonstrated that the product was neopentylglycol diisononanoate. The acid value of the product was 1.0 or less, and the saponification number was 280 to 300, and the hydroxyl value was 1.0 or less, determined according to Cosmetics Raw Material Standard: 18. Method for the Determination of an Acid Value; 16. Method for the Determination of a saponification number; and 24. Method for the Determination of a Hydroxyl Value, respectively.

Component (B): Nonionic Surfactant

Sorbitan monoisostearate: from Nihon Emulsion Co., Ltd., EMALEX SPIS-100, trademark, Lipophilic glycerin monostearate: from Nihon Emulsion Co., Ltd., EMALEX GMS-ASE, trademark, Sorbitan sesquiisostearate: from Nihon Emulsion Co., Ltd., EMALEX SPIS-150, trademark, Polyglyceryl-2 isostearate: from Kokyu Alcohol Kogyo Co., Ltd., Risorex PGIS21, trademark, Sorbitan sesquioleate: from Nihon Emulsion Co., Ltd., EMALEX SPO-100, trademark, Component (C): Oil-Soluble and/or Water-Soluble Thickener Dextrin palmitate: from Chiba Flour Milling Co., Ltd., Rheopearl KL2, trademark, (Palmitic acid/dextrin ethylhexanoate): from Chiba Flour Milling Co., Ltd., Rheopearl TT2, trademark, Inurin stearate: from Chiba Flour Milling Co., Ltd., Rheopearl ISL2, trademark, Microcrystalline wax: from Nikko Rica Corporation, Microcrystalline wax, trademark, Di(C20-40)alkyl dimer-dilinoleate: from Koster Keunen Inc., KESTER WAX K82-D, trademark, Dibutylethylhexanoylglutamide: from Ajinomoto Co., Inc., EB-21, trademark, Dibutyllauroylglutamide: from Ajinomoto Co., Inc., GP-1, trademark, Carbomer, from Nikko Chemicals Co., Ltd., Carbopol ETD2050, trademark, Xanthan gum: from Sansho Co., Ltd., KELTROL T, trademark, Hydroxyethyl cellulose: from Sumitomo Seika Chemicals Co., Ltd., HEC, trademark, (Acryloyldimethyltaurine ammonium/VP)copolymer: from Clariant, Aristoflex AVC, trademark, Component (D): Fine Particles Hydrophobicated titanium oxide: from US Cosmetic Corporation, NHS-TRI-77891, trademark, Talc: from US Cosmetic Corporation, Soft Talc, trademark, Hydrophobicated iron oxide yellow: from US Cosmetic Corporation, NHS-Y-77492, trademark, Hydrophobicated iron oxide red: from US Cosmetic Corporation, NHS-R-77491, trademark, Hydrophobicated iron oxide black: from US Cosmetic Corporation, NHS-B-77499, trademark, $TiO_2$ coated mica: from Merk & Co., Inc., Timiron Star Luster MP-1001, trademark, Hydrophobicated ultramarine: from Whittaker Clark & Daniels Inc., 7104 Ultramarine Blue, trademark, Microparticles of titanium oxide: from TAYCA Corporation, SMT-100SAS, trademark, Microparticles of zinc oxide: from TAYCA Corporation, MZ-505S, trademark, Component (E): Water Demineralized water Optional Oily Components Other than Component (A)

Hexyldecyl isostearate: from Kokyu Alcohol Kogyo Co. Ltd., ICIS, trademark,

Octyldodecyl neopentanoate: from Kokyu Alcohol Kogyo Co. Ltd., NEOLIGHT 200P, trademark, Diisostearyl malate: from Kokyu Alcohol Kogyo Co., Ltd., HAIMALATE DIS, trademark, Squalane: from Kokyu Alcohol Kogyo Co., Ltd., Olive squalane, trademark, Optional Components (Diglycerin/dilinoleic acid/hydroxystearic acid) copolymer: from Kokyu Alcohol Kogyo Co., Ltd., RISOCAST HSDA, trademark, (Polyglyceryl-2 isostearate/dimer dilinoleic acid) copolymer: from Kokyu Alcohol Kogyo Co., Ltd., HAILUCENT ISDA, trademark, Cete aryl alcohol: from Kokyu Alcohol Kogyo Co., Ltd., cetostearyl alcohol, Glycerin: from Kokyu Alcohol Kogyo Co., Ltd., Triol VE, trademark, White vaseline: from Penreco Corporate, Penreco Snow, trademark, 1,3-Butylene glycol: Daisel Chemical Industries, Ltd., 1,3-butylene glycol, Ethanol, Ethylhexyl methoxycinnamate: from ISP Corporation, ESCALOL 557, trademark, Sodium hydroxide, Spheric nylon powder: from Dow Corning Toray Co., Ltd., Torefil E505C, trademark, Crosslinked type silicone powder: from Dow Corning Toray Co., Ltd., Torefil E506C, trademark, Magnesium sulfate, Plant extract: tea extract, Perfume, Preservative: ethyl paraoxybenzoate, Moisturizing agent: hyaluronic acid Blue No. 1: from KISHI KASEI CO., LTD., Blue No. 1, trademark, Comparative Components Cyclomethicone: from Dow Corning Toray Co., Ltd., SH245 Fluid, trademark, Phenyltrimethicone: from Dow Corning Toray Co., Ltd., SH556 Fluid, trademark, Dimethicone: from GE Toshiba Silicone Co., Ltd., TSF451-100A, trademark, Dimethicone copolyol: from Evonik Goldschmidt GmbH, ABIL EM90, trademark.

Each characteristic evaluation carried out in the Examples and Comparative Examples was as follows:

Storage Stability

Water-in-oil type emulsified cosmetics, foundations, make-up bases, eye shadows, sunscreens and mascaras, as indicated in the Examples and the Comparative Examples, were prepared in accordance with the predetermined process. Three samples were prepared per each Example. Then, two of the samples were stored in a temperature-controlled bath, one at 25 degrees C. and the other at 45 degrees C., for one month. Remaining one of the samples was maintained successively at −10 degrees C., 25 degrees C. and 45 degrees C., each for 8 hours and then successively at 45 degrees C., 25 degrees C. and −10 degrees C., each for 8 hours in a temperature-controlled room. It took 48 hours per one operation. This sequential operation was repeated 5 times. The samples thus obtained were observed in respect to deterioration of appearance (occurrence of bulky particles), coloration, smelliness and separation by organoleptic assessments. As a result, in all samples, no deterioration of appearance, no coloration and no smelliness were observed. Therefore, the evaluation of storage stability was carried out only with regard to separation. Each sample was observed by eyes, and then, when there was no separation in all samples, the cosmetic was rated as "G". When the sample at one of the temperatures showed separation even if it was slight, the cosmetic was rated as "M". When the samples at two or more of the temperatures showed separation, even if it was slight, the cosmetic was rated as "B".

Applicability (Ease of Spreading)

After each of the water-in-oil type emulsified cosmetics obtained in the Examples and the Comparative Examples, foundations, make-up bases, eye shadows, sunscreens and mascaras, was applied to the skin, "applicability" was evaluated by twenty panels. For foundations, make-up bases and sunscreens, 1.0 g of each cosmetic was applied to the face. For eye shadows, 0.1 g was applied to the eyelids. For mascaras, 0.3 g was applied to the eye lashes. The indication of the evaluation results is as follows. When not less than 15 panels among 20 panels evaluated the cosmetic as "good applicability", it was rated as "G". When from 6 to 9 panels evaluated the cosmetic as "good applicability", it was rated as "M". When not more than five panels evaluated the cosmetic as "good applicability", it was rated as "B".

Stickiness

After each of the water-in-oil type emulsified cosmetics obtained in the Examples and the Comparative Examples, foundations, make-up bases, eye shadows, sunscreens and mascaras, was applied to the skin, "stickiness" was evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "no stickiness", it was rated as "G". When from 6 to 9 panels evaluated the cosmetic as "no stickiness", it was rated as "M". When not more than five panels evaluated the cosmetic as "no stickiness", it was rated as "B".

Oily Feeling

After each of the water-in-oil type emulsified cosmetics obtained in the Examples and the Comparative Examples, foundations, make-up bases, eye shadows, sunscreens and mascaras, was applied to the skin, "oily feeling" was evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "proper oily feeling", it was rated as "G". When from 6 to 9 panels evaluated the cosmetic as "proper oily feeling", it was rated as "M". When not more than five panels evaluated the cosmetic as "proper oily feeling", it was rated as "B".

Cosmetic-Holding Ability

After each of the water-in-oil type emulsified cosmetics obtained in the Examples and the Comparative Examples, foundations, make-up bases, eye shadows, sunscreens and mascaras, was applied to the skin, "cosmetic-holding ability" was evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "excellent cosmetic-holding ability", it was rated as "G". When from 6 to 9 panels evaluated the cosmetic as "excellent cosmetic-holding ability", it was rated as "M". When not more than five panels evaluated the cosmetic as "excellent cosmetic-holding ability", it was rated as "B".

Oily Sheen

After each of the water-in-oil type emulsified cosmetics obtained in the Examples and the Comparative Examples, foundations, make-up bases, eye shadows, sunscreens and mascaras, was applied to the skin, "oily sheen" was evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "no oily sheen", it was rated as "G". When from 6 to 9 panels evaluated the cosmetic as "no oily sheen", it was rated as "M". When not more than five panels evaluated the cosmetic as "no oily sheen", it was rated as "B".

Examples 1 to 6 and Comparative Examples 1 to 2

Creamy Foundation

Components (A), (B) and (C), and the optional components other than those which were water-soluble or were in a form of fine particles, indicated in Tables 1 and 2 were dissolved homogenously at 100 degrees C. to obtain a mixture, to which Component (D) and the optional components in a form of fine particles were added to make a dispersion. Then, to the dispersion thus obtained were added Component (E) and the optional components which were water-soluble to make an emulsion-dispersion. Next, the emulsion-dispersion was cooled to room temperature while stirring to prepare a creamy foundation. Units of all figures indicated in Tables 1 and 2 are % by mass.

TABLE 1

Creamy Foundation

| Component | | Ex. 1 | Ex. 2 | Ex. 3 | Ex. 4 | Ex. 5 | Ex. 6 |
|---|---|---|---|---|---|---|---|
| A | Neopentylglycol diisononanoate | 13.00 | 20.00 | 20.00 | 30.00 | 25.00 | 18.00 |
| B | Sorbitan monoisostearate | 1.00 | 0.80 | 0.80 | 1.00 | 5.00 | 0.80 |
|   | Lipophilic glycerin monostearate | — | 1.00 | 1.00 | — | 1.00 | — |
|   | Sorbitan sesquiisostearate | — | — | — | 2.00 | 1.00 | 0.50 |
| C | Dextrin palmitate | 0.50 | — | — | 2.00 | 4.00 | 1.00 |
|   | Microcrystalline wax | — | 3.00 | 3.00 | — | — | — |
|   | Di(C20-40)alkyl dimer-dilinoleate | — | — | — | 0.50 | — | — |
|   | Dibutylethylhexanoylglutamide | 0.15 | — | — | — | — | 0.10 |
|   | Dibutyllauroylglutamide | 0.15 | — | — | — | — | 0.10 |
|   | Carbomer | — | — | 0.60 | — | — | — |
|   | Xanthan gum | — | — | — | 0.60 | — | — |
|   | Hydroxyethyl cellulose | — | — | — | — | 0.20 | — |
|   | (Acryloyldimethyltaurine ammonium/VP)copolymer | — | 0.6 | — | — | — | 0.30 |
| D | Hydrophobicated titanium oxide | 7.00 | 8.00 | 8.00 | 7.50 | 7.00 | 7.50 |
|   | Talc | 1.35 | 1.30 | 1.30 | 2.00 | 1.35 | 2.00 |
|   | Hydrophobicated iron oxide yellow | 1.20 | 1.30 | 1.30 | 1.25 | 1.20 | 1.25 |
|   | Hydrophobicated Bengara | 0.30 | 0.26 | 0.26 | 0.28 | 0.30 | 0.28 |
|   | Hydrophobicated iron oxide black | 0.15 | 0.11 | 0.11 | 0.18 | 0.15 | 0.18 |
| E | Water | 62.50 | 56.63 | 56.48 | 45.69 | 42.80 | 56.29 |
| Optional Component | Hexyldecyl isostearate | 5.00 | — | — | — | 2.00 | — |
|   | Squalane | — | 2.00 | 2.00 | — | 2.00 | 1.00 |
|   | Cyclomethicone | — | — | — | — | — | 2.00 |
|   | Phenyltrimethicone | — | — | — | — | — | 1.00 |
|   | Dimethicone | — | — | — | — | — | 1.00 |
|   | Dimethicone copolyol | — | — | — | — | — | — |
|   | (Diglycerin/dilinoloic acid/hydroxystearic acid) copolymer | 2.00 | 1.00 | 1.00 | — | 3.00 | 1.20 |
|   | Cetearyl alcohol | — | 1.00 | 1.00 | — | — | — |
|   | Glycerin | 3.00 | — | — | 5.00 | — | — |
|   | 1,3-Butylene glycol | 1.20 | — | — | — | 3.00 | 5.00 |
|   | Ethylhexyl methoxycinnamate | 1.00 | 3.00 | 3.00 | — | — | — |
|   | Sodium hydroxide | — | — | 0.15 | — | — | — |
|   | Spheric nylon powder | 0.50 | — | — | — | 1.00 | — |
|   | Crosslinked type silicone powder | — | — | — | 2.00 | — | — |
|   | Magnesium sulfate | — | — | — | — | — | 0.50 |
|   | Preservative | trace amount | trace amount | trace amount | trace amount | trace amount | trace amount |
| Evaluation | Storage stability | G | G | G | G | G | G |
|   | Applicability (ease of spreading) | G | G | G | G | G | G |
|   | Stickiness | G | G | G | G | G | G |
|   | Oily feeling | G | G | G | G | G | G |
|   | Cosmetic-holding ability | G | G | G | G | G | G |
|   | Oily sheen | G | G | G | G | G | G |

TABLE 2

Creamy Foundation

| Component | | Com. Ex. 1 | Com. Ex. 2 |
|---|---|---|---|
| Comparative A | Cyclomethicone | 13.00 | 20.00 |
|   | Phenyltrimethicone | — | 5.00 |
|   | Dimethicone | 5.00 | 5.00 |
| Comparative B | Dimethicone copolyol | 1.00 | 3.00 |
| C | Dextrin palmitate | 0.5 | 2.00 |
|   | Microcrystalline wax | — | — |
|   | Di(C20-40)alkyl dimer-dilinoleate | — | 0.50 |
|   | Dibutylethylhexanoylglutamide | 0.15 | — |
|   | Dibutyllauroylglutamide | 0.15 | — |
|   | Carbomer | — | — |
|   | Xanthan gum | — | 0.60 |
|   | Hydroxyethyl cellulose | — | — |
|   | (Acryloyldimethyltaurine ammonium/VP) copolymer | — | — |
| D | Hydrophobicated titanium oxide | 7.00 | 7.50 |
|   | Talc | 1.35 | 2.00 |
|   | Hydrophobicated iron oxide yellow | 1.20 | 1.25 |

TABLE 2-continued

Creamy Foundation

| | Component | Com. Ex. 1 | Com. Ex. 2 |
|---|---|---|---|
| E | Hydrophobicated Bengara | 0.30 | 0.28 |
|   | Hydrophobicated iron oxide black | 0.15 | 0.18 |
|   | Water | 62.50 | 45.69 |
| Optional Component | Hexyldecyl isostearate | — | — |
|   | Squalane | — | — |
|   | (Diglycerin/dilinoleic acid/hydroxystearic acid) copolymer | 2.00 | — |
|   | Cetearyl alcohol | — | — |
|   | Glycerin | 3.00 | 5.00 |
|   | 1,3-Butylene glycol | 1.20 | — |
|   | Ethylhexyl methoxycinnamate | 1.00 | — |
|   | Sodium hydroxide | — | — |
|   | Spheric nylon powder | 0.50 | — |
|   | Crosslinked type silicone powder | — | 2.00 |
|   | Magnesium sulfate | — | — |
|   | Preservative | trace amount | trace amount |
| Evaluation | Storage stability | G | G |
|   | Applicability (ease of spreading) | G | G |
|   | Stickiness | M | B |
|   | Oily feeling | M | M |
|   | Cosmetic-holding ability | M | B |
|   | Oily sheen | B | B |

Examples 7 to 8 and Comparative Example 3

Liquid Foundation

The procedures of Example 1 were repeated, except that Components (A), (B), (C), (D) and (E), and the optional components indicated in Tables 3 and 4 were used, to prepare a liquid foundation. Units of all figures indicated in Tables 3 and 4 are % by mass.

TABLE 3

Liquid foundation

| | Component | Ex. 7 | Ex. 8 |
|---|---|---|---|
| A | Neopentylglycol diisononanoate | 20.00 | 18.00 |
| B | Sorbitan monoisostearate | 1.00 | — |
|   | Sorbitan sesquiisostearate | — | 1.00 |
|   | Polyglyceryl-2 isostearate | 1.00 | — |
| C | Dextrin palmitate | 0.30 | — |
|   | Di(C20-40)alkyl dimer-dilinoleate | — | 0.30 |
|   | Dibutyllauroylglutamide | — | 0.20 |
| D | Hydrophobicated titanium oxide | 8.00 | 7.00 |
|   | Talc | 4.00 | 5.00 |
|   | Hydrophobicated iron oxide yellow | 1.50 | 1.20 |
|   | Hydrophobicated Bengara | 0.40 | 0.30 |
|   | Hydrophobicated iron oxide black | 0.17 | 0.14 |
| E | Water | 46.13 | 54.86 |
| Optional Component | Octyldodecyl neopentanoate | 2.00 | — |
|   | Squalane | 2.00 | — |
|   | Cyclomethicone | — | 3.00 |
|   | Phenyltrimethicone | — | — |
|   | Dimethicone | — | 1.00 |
|   | Dimethicone copolyol | — | — |
|   | (Diglycerin/dilinoleic acid/hydroxystearic acid) copolymer | 1.50 | 1.00 |
|   | 1,3-Butylene glycol | — | 4.00 |
|   | Ethanol | 8.00 | — |
|   | Ethylhexyl methoxycinnamate | 2.00 | 2.00 |
|   | Crosslinked type silicone powder | 2.00 | 1.00 |
|   | Preservative | trace amount | trace amount |

TABLE 3-continued

Liquid foundation

| | Component | Ex. 7 | Ex. 8 |
|---|---|---|---|
| Evaluation | Storage stability | G | G |
|   | Applicability (ease of spreading) | G | G |
|   | Stickiness | G | G |
|   | Oily feeling | G | G |
|   | Cosmetic-holding ability | G | G |
|   | Oily sheen | G | G |

TABLE 4

Liquid foundation

| | Component | Com. Ex. 3 |
|---|---|---|
| Comparative A | Cyclomethicone | 19.00 |
|   | Phenyltrimethicone | — |
|   | Dimethicone | 5.00 |
| Comparative B | Dimethicone copolyol | 2.00 |
| C | Dextrin palmitate | 0.30 |
|   | Di(C20-40)alkyl dimer-dilinoleate | — |
|   | Dibutyllauroylglutamide | — |
| D | Hydrophobicated titanium oxide | 8.00 |
|   | Talc | 4.00 |
|   | Hydrophobicated iron oxide yellow | 1.50 |
|   | Hydrophobicated Bengara | 0.40 |
|   | Hydrophobicated iron oxide black | 0.17 |
| E | Water | 46.13 |
| Optional Component | Octyldodecyl neopentanoate | — |
|   | Squalane | — |
|   | (Diglycerin/dilinoleic acid/hydroxystearic acid) copolymer | 1.50 |
|   | 1,3-Butylene glycol | — |
|   | Ethanol | 8.00 |
|   | Ethylhexyl methoxycinnamate | 2.00 |
|   | Crosslinked type silicone powder | 2.00 |
|   | Preservative | trace amount |
| Evaluation | Storage stability | G |
|   | Applicability (ease of spreading) | M |
|   | Stickiness | M |
|   | Oily feeling | M |
|   | Cosmetic-holding ability | M |
|   | Oily sheen | B |

Examples 9 to 10 and Comparative Example 4

Cosmetic Base

The procedures of Example 1 were repeated, except that Components (A), (B), (C), (D) and (E), and the optional components indicated in Tables 5 and 6 were used, to prepare a cosmetic base. Units of all figures indicated in Tables 5 and 6 are % by mass.

TABLE 5

Cosmetic base

| | Component | Ex. 9 | Ex. 10 |
|---|---|---|---|
| A | Neopentylglycol diisononanoate | 20.00 | 15.00 |
| B | Sorbitan monoisostearate | 1.00 | — |
|   | Sorbitan oleate | — | 1.00 |
|   | Sorbitan sesquiisostearate | 0.20 | — |
| C | Dextrin palmitate | 1.00 | 1.00 |
|   | Dibutylethylhexanoylglutamide | 0.05 | — |
|   | Dibutyllauroylglutamide | 0.05 | — |
| D | Hydrophobicated titanium oxide | 1.00 | 0.50 |
|   | Talc | 2.50 | 3.00 |
|   | TiO2 coated mica | 3.00 | 2.00 |

TABLE 5-continued

Cosmetic base

| | Component | Ex. 9 | Ex. 10 |
|---|---|---|---|
| E | Water | 62.90 | 63.40 |
| Optional Component | Hexyldecyl isostearate | 2.00 | — |
| | Squalane | — | 5.00 |
| | Cyclomethicone | — | 5.00 |
| | Phenyltrimethicone | — | — |
| | Dimethicone | — | — |
| | Dimethicone copolyol | — | — |
| | (Diglycerin/dilinoleic acid/hydroxystearic acid) copolymer | 2.00 | 1.00 |
| | Cetearyl alcohol | 1.00 | — |
| | White vaseline | — | 2.00 |
| | Glycerin | 2.00 | 1.00 |
| | 1,3-Butylene glycol | 1.20 | — |
| | Plant extract | 0.10 | 0.10 |
| | Perfume | trace amount | trace amount |
| | Preservative | trace amount | trace amount |
| Evaluation | Storage stability | G | G |
| | Applicability (ease of spreading) | G | G |
| | Stickiness | G | G |
| | Oily feeling | G | G |
| | Cosmetic-holding ability | G | G |
| | Oily sheen | G | G |

TABLE 6

Cosmetic base

| | Component | Com. Ex. 4 |
|---|---|---|
| Comparative A | Cyclomethicone | 22.00 |
| | Phenyltrimethicone | — |
| | Dimethicone | — |
| Comparative B | Dimethicone copolyol | 1.20 |
| C | Dextrin palmitate | 1.00 |
| | Dibutylethylhexanoylglutamide | 0.05 |
| | Dibutyllauroylglutamide | 0.05 |
| D | Hydrophobicated titanium oxide | 1.00 |
| | Talc | 2.50 |
| | TiO2 coated mica | 3.00 |
| E | Water | 62.90 |
| Optional Component | Hexyldecyl isostearate | — |
| | Squalane | — |
| | (Diglycerin/dilinoleic acid/hydroxystearic acid) copolymer | 2.00 |
| | Cetearyl alcohol | 1.00 |
| | White vaseline | — |
| | Glycerin | 2.00 |
| | 1,3-Butylene glycol | 1.20 |
| | Plant extract | 0.10 |
| | Perfume | trace amount |
| | Preservative | trace amount |
| Evaluation | Storage stability | G |
| | Applicability (ease of spreading) | G |
| | Stickiness | M |
| | Oily feeling | M |
| | Cosmetic-holding ability | M |
| | Oily sheen | M |

TABLE 7

Creamy eye shadow

| | Component | Ex. 11 |
|---|---|---|
| A | Neopentylglycol diisononanoate | 11.00 |
| B | Sorbitan monoisostearate | 1.00 |
| | Sorbitan oleate | — |
| | Sorbitan sesquiisostearate | 0.20 |
| C | Dextrin palmitate | 2.50 |
| D | Hydrophobicated ultramarine | 8.00 |
| | Hydrophobicated iron oxide black | 1.00 |
| | TiO2 coated mica | 0.80 |
| E | Water | 59.30 |
| Optional Component | Hexyldecyl isostearate | 1.00 |
| | Squalane | 1.00 |
| | Diisostearyl malate | 5.00 |
| | Cyclomethicone | 2.00 |
| | Phenyltrimethicone | — |
| | Dimethicone | — |
| | Dimethicone copolyol | — |
| | (Diglycerin/dilinoleic acid/hydroxystearic acid) copolymer | 1.00 |
| | Glycerin | 3.00 |
| | 1,3-Butylene glycol | 3.00 |
| | Magnesium sulfate | 0.20 |
| | Preservative | trace amount |
| Evaluation | Storage stability | G |
| | Applicability (ease of spreading) | G |
| | Stickiness | G |
| | Oily feeling | G |
| | Cosmetic-holding ability | G |
| | Oily sheen | G |

TABLE 8

Creamy eye shadow

| | Component | Com. Ex. 5 |
|---|---|---|
| Comparative A | Cyclomethicone | 15 |
| | Phenyltrimethicone | — |
| | Dimethicone | 5 |
| Comparative B | Dimethicone copolyol | 1.2 |
| C | Dextrin palmitate | 2.5 |
| D | Hydrophobicated ultramarine | 8 |
| | Hydrophobicated iron oxide black | 1 |
| | TiO2 coated mica | 0.8 |
| E | Water | 59.3 |
| Optional Component | Hexydecyl isostearate | — |
| | Squalane | — |
| | Diisostearyl malate | — |
| | (Diglycerin/dilinoleic acid/hydroxystearic acid) copolymer | 1 |
| | Glycerin | 3 |
| | 1,3-Butylene glycol | 3 |
| | Magnesium sulfate | 0.2 |
| | Preservative | trace amount |
| Evaluation | Storage stability | G |
| | Applicability (ease of spreading) | G |
| | Stickiness | M |
| | Oily feeling | M |
| | Cosmetic-holding ability | M |
| | Oily sheen | M |

Example 11 and Comparative Example 5

Creamy Eye Shadow

The procedures of Example 1 were repeated, except that Components (A), (B), (C), (D) and (E), and the optional components indicated in Tables 7 and 8 were used, to prepare a creamy eye shadow. Units of all figures indicated in Tables 7 and 8 are % by mass.

Example 12

Milky Emulsion Type Sunscreen

Components (A), (B) and (C), and the optional components other than those which were water-soluble, indicated in Table 9 were dissolved homogenously at 100 degrees C. to obtain a mixture, to which Component (D) was added to make a dispersion. Then, Component (E) and the optional components which were water-soluble were added to the dispersion thus obtained to make an emulsion-dispersion.

The emulsion-dispersion thus obtained was cooled to room temperature while stirring to prepare a milky emulsion type sunscreen.

Example 13 and Comparative Example 6

Creamy Sunscreen

Use were made of Components (A), (B), (C), (D) and (E), and the optional components indicated in Tables 9 and 10. The procedures of Example 12 were repeated to prepare a creamy sunscreen. Units of all figures indicated in Tables 9 and 10 are % by mass.

TABLE 9

Ceamy sunscreen

| Component | | Ex. 12 | Ex. 13 |
|---|---|---|---|
| A | Neopentylglycol diisononanoate | 20.00 | 25.00 |
| B | Sorbitan monoisostearate | 1.00 | — |
|   | Sorbitan oleate | — | 1.00 |
|   | Sorbitan sesquiisostearate | 0.20 | — |
| C | Dextrin palmitate | 2.50 | 2.00 |
|   | Microcrystalline wax |  | 2.00 |
| D | Microparticles of titanium oxide | 1.00 | 5.00 |
|   | Microparticles of zinc oxide | — | 5.00 |
| E | Water | 63.10 | 44.50 |
| Optional Component | Hexyldecyl isostearate | 1.00 | — |
|   | Squalane | 2.00 | 5.00 |
|   | Cyclomethicone | — | 4.00 |
|   | Phenyltrimethicone | — | — |
|   | Dimethicone | — | 1.00 |
|   | Dimethicone copolyol | — | — |
|   | (Diglycerin/dilinoleic acid/hydroxystearic acid) copolymer | 3.00 | 2.00 |
|   | Cetearyl alcohol | — | 1.50 |
|   | Ethylhexyl methoxycinnamate | 3.00 | — |
|   | Glycerin | 2.00 | 2.00 |
|   | 1,3-Butylene glycol | 1.20 | — |
|   | Preservative | trace amount | trace amount |
| Evaluation | Storage stability | G | G |
|   | Applicability (ease of spreading) | G | G |
|   | Stickiness | G | G |
|   | Oily feeling | G | G |
|   | Cosmetic-holding ability | G | G |
|   | Oily sheen | G | G |

TABLE 10

Creamy sunscreen

| Component | | Com. Ex. 6 |
|---|---|---|
| Comparative A | Cyclomethicone | 28.00 |
|   | Phenyltrimethicone | — |
|   | Dimethicone | 7.00 |
| Comparative B | Dimethicone copolyol | 1.00 |
| C | Dextrin palmitate | 2.00 |
|   | Microcrystalline wax | 2.00 |
| D | Microparticles of titanium oxide | 5.00 |
|   | Microparticles of zinc oxide | 5.00 |
| E | Water | 44.50 |
| Optional Component | Hexyldecyl isostearate | — |
|   | Squalane | — |
|   | (Diglycerin/dilinoleic acid/hydroxystearic acid) copolymer | 2.00 |
|   | Cetearyl alcohol | 1.50 |
|   | Ethylhexyl methoxycinnamate | — |

TABLE 10-continued

Creamy sunscreen

| Component | | Com. Ex. 6 |
|---|---|---|
|   | Glycerin | 2.00 |
|   | 1,3-Butylene glycol | — |
|   | Preservative | trace amount |
| Evaluation | Storage stability | G |
|   | Applicability (ease of spreading) | G |
|   | Stickiness | M |
|   | Oily feeling | M |
|   | Cosmetic-holding ability | B |
|   | Oily sheen | M |

Example 14 and Comparative Example 7

Emulsified Mascara

The procedures of Example 1 were repeated, except that Components (A), (B), (C), (D) and (E), and the optional components indicated in Tables 11 and 12 were used, to prepare an emulsified mascara. Units of all figures indicated in Tables 11 and 12 are % by mass.

TABLE 11

Emulsified mascara

| Component | | Ex. 14 |
|---|---|---|
| A | Neopentylglycol diisononanoate | 20.00 |
| B | Sorbitan monoisostearate | 1.00 |
|   | Sorbitan oleate | — |
|   | Sorbitan sesquiisostearate | 0.20 |
| C | Inurin stearate | 2.50 |
|   | (Acryloyldimethyltaurine ammonium/VP)copolymer | 0.20 |
| D | Hydrophobicated iron oxide black | 10.50 |
| E | Water | 30.50 |
| Optional Component | Hexyldecyl isostearate | 1.00 |
|   | Squalane | 2.00 |
|   | Cyclomethicone | 1.00 |
|   | Phenyltrimethicone | — |
|   | Dimethicone | 1.00 |
|   | Dimethicone copolyol | — |
|   | (Diglycerin/dilinoleic acid/hydroxystearic acid) copolymer | 3.00 |
|   | (Polyglyceryl-2 isostearate/dimer dilinoleic acid) copolymer | 20.00 |
|   | Blue No. 1 | 2.10 |
|   | 1,3-Butylene glycol | 2.00 |
|   | Ethanol | 3.00 |
|   | Moisturizing agent | trace amount |
|   | Preservative | trace amount |
| Evaluation | Storage stability | G |
|   | Applicability (ease of spreading) | G |
|   | Cosmetic-holding ability | G |

TABLE 12

Emulsified mascara

| Component | | Com. Ex. 7 |
|---|---|---|
| Comparative A | Cyclomethicone | 20.00 |
|   | Phenyltrimethicone | — |
|   | Dimethicone | 5.00 |
| Comparative B | Dimethicone copolyol | 1.20 |
| C | Inurin stearate | 2.50 |
|   | (Acryloyldimethyltaurine ammonium/VP)copolymer | 0.20 |
| D | Hydrophobicated iron oxide black | 10.50 |
| E | Water | 30.50 |

TABLE 12-continued

Emulsified mascara

| Component | | Com. Ex. 7 |
|---|---|---|
| Optional Component | Hexyldecyl isostearate | — |
| | squalane | — |
| | (Diglycerin/dilinoleic acid/hydroxystearic acid) copolymer | 3.00 |
| | (Polyglyceryl-2 isostearate/dimer dilinoleic acid) copolymer | 20.00 |
| | Blue No. 1 | 2.10 |
| | 1,3-Butylene glycol | 2.00 |
| | Ethanol | 3.00 |
| | Moisturizing agent | trace amount |
| | Preservative | trace amount |
| Evaluation | Storage stability | G |
| | Applicability (ease of spreading) | M |
| | Cosmetic-holding ability | G |

In Examples 1 to 6, creamy foundations were prepared, wherein the amount of Component (A) was varied. The evaluation results were good in all of the Examples. It was found that good evaluation results were obtained even if various substances were used as Components (B) and (C) within the present invention. In Example 6, use was made of the predetermined amount of the silicone type oil agent which was said, in the prior art, to be poor in applicability and to easily induce an oily sheen after application. Upon use of the silicone type oil agent in the present cosmetic, it was found that the drawbacks of the oil agent were overcome and that the cosmetic exhibits good evaluation results. There were prepared liquid foundations in Examples 7 and 8, and Comparative Example 3; cosmetic bases in Examples 9 and 10, and Comparative Example 4; creamy eye shadows in Example 11 and Comparative Example 5; a milky emulsion type sunscreen in Example 12; creamy sunscreens in Example 13 and Comparative Example 6; and emulsified mascaras in Example 14 and Comparative Example 7. All the cosmetics of the present invention exhibited considerably good evaluation results. Meanwhile, in Comparative Examples where the prior art silicone type oil agent was used, good evaluation results were not obtained.

Comparative Examples 8 and 9

The procedures of Example 1 were repeated, except that Components (A), (B), (C) and (E), and the optional components indicated in Table 13 were used, to prepare a creamy foundation. Units of all figures indicated in Table 13 are % by mass.

TABLE 13

Creamy foundation

| Component | | Com. Ex. 8 | Com. Ex. 9 |
|---|---|---|---|
| Comparative A | Dimethicone | 10.00 | — |
| A | Neopentylglycol diisononanoate | — | 10.00 |
| Comparative B | Crosslinked alkyl polyether modified silicone | 2.00 | 2.00 |
| B | Polyglyceryl monoisostearate | 0.50 | 0.50 |
| C | Dextrin palmitate | 0.10 | 0.10 |
| | Cationic crosslinked polymer | 0.40 | 0.40 |
| D | Hydrophobicated titanium oxide | — | — |
| | Talc | — | — |
| | Hydrophobicated iron oxide yellow | — | — |
| | Hydrophobicated Bengara | — | — |
| | Hydrophobicated iron oxide black | — | — |
| E | Water | 77.00 | 77.00 |
| Optional Component | Squalane | 10.00 | 10.00 |
| Evaluation | Storage stability | M | B |
| | Applicability (ease of spreading) | B | B |
| | Stickiness | M | M |
| | Oily feeling | M | M |
| | Cosmetic-holding ability | M | M |
| | Oily sheen | B | M |

The cosmetic in Comparative Example 8 is the water-in-oil type emulsified cosmetic described in Example 12 in Japanese Patent Application Laid-Open 2008-127,306. The evaluation result was poor, similarly to those of the prior art cosmetics containing a silicone type oil agent. In Comparative Example 9, dimethicone used in Comparative Example 8 was replaced with neopentylglycol diisononanoate which was Component (A) in the present invention. The evaluation results were somewhat improved, but good evaluation result was not obtained because a large quantity of the silicone type surfactant was contained, so that component (A) was not able to be sufficiently emulsified.

Examples 15 to 19 and Comparative Examples 10 to 11

The procedures of Example 1 were repeated, except that Components (A), (B), (C), (D) and (E), and the optional components indicated in Table 14 were used, to prepare a creamy foundation. Units of all figures indicated in Table 14 are % by mass.

TABLE 14

Creamy foundation

| Component | | Ex. 2 | Ex. 15 | Ex. 16 | Ex. 17 | Ex. 18 | Ex. 19 | Com. EX. 10 | Com. Ex. 11 |
|---|---|---|---|---|---|---|---|---|---|
| A | Neopentylglycol diisononanoate | 20.00 | 10.00 | 15.00 | 30.00 | 40.00 | 50.00 | 5.00 | 65.00 |
| B | Sorbitan monoisostearate | 0.80 | 0.90 | 0.85 | 0.70 | 0.60 | 0.50 | 0.95 | 0.35 |
| | Lipophilic glycerin monostearate | 1.00 | 1.13 | 1.06 | 0.88 | 0.75 | 0.63 | 1.18 | 0.44 |
| | Sorbitan sesquiisostearate | — | — | — | — | — | — | — | — |
| C | Dextrin palmitate | — | — | — | — | — | — | — | — |
| | Microcrystalline wax | 3.00 | 3.38 | 3.19 | 2.63 | 2.25 | 1.88 | 3.57 | 1.31 |
| | Di(C20-40)alkyl dimer-dilinoleate | — | — | — | — | — | — | — | — |
| | Dibutylethylhexanoylglutamide | — | — | — | — | — | — | — | — |
| | Dibutyllauroylglutamide | — | — | — | — | — | — | — | — |
| | Carbomer | — | — | — | — | — | — | — | — |
| | Xanthan gum | — | — | — | — | — | — | — | — |

TABLE 14-continued

Creamy foundation

| Component | | Ex. 2 | Ex. 15 | Ex. 16 | Ex. 17 | Ex. 18 | Ex. 19 | Com. EX. 10 | Com. Ex. 11 |
|---|---|---|---|---|---|---|---|---|---|
| | Hydroxyethyl cellulose | — | — | — | — | — | — | — | — |
| | (Acryloyldimethyltaurine ammonium/VP)copolymer | 0.6 | 0.88 | 0.64 | 0.53 | 0.45 | 0.38 | 0.72 | 0.26 |
| D | Hydrophobicated titanium oxide | 8.00 | 9.00 | 8.50 | 7.00 | 6.00 | 5.00 | 9.50 | 3.50 |
| | Talc | 1.30 | 1.46 | 1.38 | 1.14 | 0.98 | 0.81 | 1.54 | 0.57 |
| | Hydrophobicated iron oxide yellow | 1.30 | 1.46 | 1.38 | 1.14 | 0.98 | 0.81 | 1.54 | 0.57 |
| | Hydrophobicated Bengara | 0.26 | 0.29 | 0.28 | 0.23 | 0.2 | 0.16 | 0.31 | 0.11 |
| | Hydrophobicated iron oxide black | 0.11 | 0.12 | 0.12 | 0.1 | 0.08 | 0.07 | 0.13 | 0.05 |
| E | Water | 56.63 | 63.69 | 60.16 | 49.51 | 42.46 | 35.37 | 67.25 | 24.79 |
| Optional Component | Hexyldecyl isostearate | — | — | — | — | — | — | — | — |
| | Squalane | 2.00 | 2.25 | 2.13 | 1.75 | 1.50 | 1.25 | 2.38 | 0.88 |
| | Cyclomethicone | — | — | — | — | — | — | — | — |
| | Phenyltrimethicone | — | — | — | — | — | — | — | — |
| | Dimethicone | — | — | — | — | — | — | — | — |
| | Dimethicone copolyol | — | — | — | — | — | — | — | — |
| | (Diglycerin/dilinoleic acid/hydroxystearic acid) copolymer | 1.00 | 1.13 | 1.06 | 0.88 | 0.75 | 0.63 | 1.18 | 0.43 |
| | Cetearyl alcohol | 1.00 | 1.13 | 1.06 | 0.88 | 0.75 | 0.63 | 1.18 | 0.43 |
| | Glycerin | — | — | — | — | — | — | — | — |
| | 1,3-Butylene glycol | — | — | — | — | — | — | — | — |
| | Ethylhexyl methoxycinnamate | 3.00 | 3.38 | 3.19 | 2.63 | 2.25 | 1.88 | 3.57 | 1.31 |
| | Sodium hydroxide | — | — | — | — | — | — | — | — |
| | Spheric nylon powder | — | — | — | — | — | — | — | — |
| | Crosslinked type silicone powder | — | — | — | — | — | — | — | — |
| | Magnesium sulfate | — | — | — | — | — | — | — | — |
| | Preservative | trace amount | trace amount | trace amount | trace amount | trace amount | trace amount | trace amount | trace amount |
| Evaluation | Storage stability | G | G | G | G | G | G | B | B |
| | Applicability (ease of spreading) | G | G | G | G | G | G | B | B |
| | Stickiness | G | G | G | G | G | G | B | B |
| | Oily feeling | G | G | G | G | G | G | B | B |
| | Cosmetic-holding ability | G | G | G | G | G | G | B | B |
| | Oily sheen | G | G | G | G | G | G | B | B |

In Examples 15 to 19 and Comparative Examples 10 to 11, the ratio of Component (A) was varied, on the basis of the composition in Example 2. Now, in each example or comparative Example, the ratio among the components other than (A) was adjusted to be same as that in Example 2. Within the present invention, good evaluation results were obtained.

Examples 20 to 23 and Comparative Examples 12 to 13

The procedures of Example 1 were repeated, except that Components (A), (B), (C), (D) and (E), and the optional components indicated in Table 15 were used, to prepare a creamy foundation. Units of all figures indicated in Table 15 are % by mass.

TABLE 15

Creamy foundation

| Component | | Ex. 2 | Ex. 20 | EX. 21 | EX. 22 | Ex. 23 | Com. EX. 12 | Com. EX. 13 |
|---|---|---|---|---|---|---|---|---|
| A | Neopentylglycol diisononanoate | 20.00 | 20.16 | 19.55 | 18.94 | 18.33 | 20.20 | 17.52 |
| B | Sorbitan monoisostearate | 0.80 | 0.44 | 1.78 | 3.11 | 4.44 | 0.36 | 6.22 |
| | Lipophilic glycerin monostearate | 1.00 | 0.56 | 2.22 | 3.89 | 5.56 | 0.44 | 7.78 |
| | Sorbitan sesquiisostearate | — | — | — | — | — | — | — |
| C | Dextrin palmitate | — | — | — | — | — | — | — |
| | Microcrystalline wax | 3.00 | 3.02 | 2.93 | 2.84 | 2.75 | 3.03 | 2.63 |
| | Di(C20-40)alkyl dimer-dilinoleate | — | — | — | — | — | — | — |
| | Dibutylethylhexanoylglutamide | — | — | — | — | — | — | — |
| | Dibutyllauroylglutamide | — | — | — | — | — | — | — |
| | Carbomer | — | — | — | — | — | — | — |
| | Xanthan gum | — | — | — | — | — | — | — |
| | Hydroxyethyl cellulose | — | — | — | — | — | — | — |
| | (Acryloyldimethyltaurine ammonium/VP)copolymer | 0.60 | 0.61 | 0.58 | 0.56 | 0.54 | 0.61 | 0.51 |
| D | Hydrophobicated titanium oxide | 8.00 | 8.07 | 7.82 | 7.58 | 7.33 | 8.08 | 7.01 |
| | Talc | 1.30 | 1.31 | 1.27 | 1.23 | 1.19 | 1.31 | 1.14 |
| | Hydrophobicated iron oxide yellow | 1.30 | 1.31 | 1.27 | 1.23 | 1.19 | 1.31 | 1.14 |
| | Hydrophobicated Bengara | 0.26 | 0.26 | 0.25 | 0.25 | 0.24 | 0.26 | 0.23 |
| | Hydrophobicated iron oxide black | 0.11 | 0.11 | 0.11 | 0.1 | 0.1 | 0.11 | 0.1 |

TABLE 15-continued

Creamy foundation

| Component | | Ex. 2 | Ex. 20 | EX. 21 | EX. 22 | Ex. 23 | Com. EX. 12 | Com. EX. 13 |
|---|---|---|---|---|---|---|---|---|
| E | Water | 56.63 | 57.09 | 55.37 | 53.64 | 51.91 | 57.22 | 49.58 |
| Optional Component | Hexyldecyl isostearate | — | — | — | — | — | — | — |
| | Squalane | 2.00 | 2.02 | 1.96 | 1.89 | 1.83 | 2.02 | 1.75 |
| | Cyclomethicone | — | — | — | — | — | — | — |
| | Phenyltrimethicone | — | — | — | — | — | — | — |
| | Dimethicone | — | — | — | — | — | — | — |
| | Dimethicone copolyol | — | — | — | — | — | — | — |
| | (Diglycerin/dilinoleic acid/ hydroxystearic acid) copolymer | 1.00 | 1.01 | 0.98 | 0.95 | 0.92 | 1.01 | 0.88 |
| | Cetearyl alcohol | 1.00 | 1.01 | 0.98 | 0.95 | 0.92 | 1.01 | 0.88 |
| | Glycerin | — | — | — | — | — | — | — |
| | 1,3-Butylene glycol | — | — | — | — | — | — | — |
| | Ethylhexyl methoxycinnamate | 3.00 | 3.02 | 2.93 | 2.84 | 2.75 | 3.03 | 2.63 |
| | Sodium hydroxide | — | — | — | — | — | — | — |
| | Spheric nylon powder | — | — | — | — | — | — | — |
| | Crosslinked type silicone powder | — | — | — | — | — | — | — |
| | Magnesium sulfate | — | — | — | — | — | — | — |
| | Preservative | trace amount | trace amount | trace amount | trace amount | trace amount | trace amount | trace amount |
| Evaluation | Storage stability | G | G | G | G | G | B | B |
| | Applicability (ease of spreading) | G | G | G | G | G | B | B |
| | Stickiness | G | G | G | G | G | B | B |
| | Oily feeling | G | G | G | G | G | B | B |
| | Cosmetic-holding ability | G | G | G | G | G | B | B |
| | Oily sheen | G | G | G | G | G | B | B |

In Examples 20 to 23 and Comparative Examples 12 to 13, the ratio of Component (B) was varied, on the basis of the composition in Example 2. Now, in each Example or Comparative Example, the ratio among the components other than (B) was adjusted to be same as that in Example 2. Within the present invention, good evaluation results were obtained.

Examples 24 to 28 and Comparative Examples 14 to 15

The procedures of Example 1 were repeated, except that Components (A), (B), (C), (D) and (E), and the optional components indicated in Table 16 were used, to prepare a creamy foundation. Units of all figures indicated in Table 16 are % by mass.

TABLE 16

Creamy foundation

| Component | | Ex. 2 | Ex. 24 | Ex. 25 | Ex. 26 | Ex. 27 | Ex. 28 | Com. EX. 14 | Com. EX. 15 |
|---|---|---|---|---|---|---|---|---|---|
| A | Neopentylglycol diisononanoate | 20.00 | 20.68 | 20.33 | 19.71 | 19.09 | 18.67 | 20.71 | 18.05 |
| B | Sorbitan monoisostearate | 0.80 | 0.83 | 0.81 | 0.79 | 0.76 | 0.75 | 0.83 | 0.72 |
| | Lipophilic glycerin monostearate | 1.00 | 1.03 | 1.02 | 0.99 | 0.95 | 0.93 | 1.04 | 0.90 |
| | Sorbitan sesquiisostearate | — | — | — | — | — | — | — | — |
| C | Dextrin palmitate | — | — | — | — | — | — | — | — |
| | Microcrystalline wax | 3.00 | 0.25 | 1.67 | 4.17 | 6.67 | 8.33 | 0.17 | 10.83 |
| | Di(C20-40)alkyl dimer-dilinoleate | — | — | — | — | — | — | — | — |
| | Dibutylethylhexanoylglutamide | — | — | — | — | — | — | — | — |
| | Dibutyllauroylglutamide | — | — | — | — | — | — | — | — |
| | Carbomer | — | — | — | — | — | — | — | — |
| | Xanthan gum | — | — | — | — | — | — | — | — |
| | Hydroxyethyl cellulose | — | — | — | — | — | — | — | — |
| | (Acryloyldimethyltaurine ammonium/VP)copolymer | 0.60 | 0.05 | 0.33 | 0.83 | 1.33 | 1.67 | 0.03 | 2.17 |
| D | Hydrophobicated titanium oxide | 8.00 | 8.27 | 8.13 | 7.88 | 7.63 | 7.47 | 8.28 | 7.22 |
| | Talc | 1.30 | 1.34 | 1.32 | 1.28 | 1.24 | 1.21 | 1.35 | 1.17 |
| | Hydrophobicated iron oxide yellow | 1.30 | 1.34 | 1.32 | 1.28 | 1.24 | 1.21 | 1.35 | 1.17 |
| | Hydrophobicated Bengara | 0.26 | 0.27 | 0.26 | 0.26 | 0.25 | 0.24 | 0.27 | 0.23 |
| | Hydrophobicated iron oxide black | 0.11 | 0.11 | 0.11 | 0.11 | 0.10 | 0.10 | 0.11 | 0.10 |
| E | Water | 56.63 | 58.58 | 57.58 | 55.79 | 53.99 | 52.89 | 58.60 | 51.13 |
| Optional Component | Hexyldecyl isostearate | — | — | — | — | — | — | — | — |
| | Squalane | 2.00 | 2.09 | 2.03 | 1.97 | 1.99 | 1.87 | 2.07 | 1.80 |
| | Cyclomethicone | — | — | — | — | — | — | — | — |
| | Phenyltrimethicone | — | — | — | — | — | — | — | — |
| | Dimethicone | — | — | — | — | — | — | — | — |
| | Dimethicone copolyol | — | — | — | — | — | — | — | — |
| | (Diglycerin/dilinoleic acid/ hydroxystearic acid) copolymer | 1.00 | 1.03 | 1.02 | 0.99 | 0.95 | 0.93 | 1.04 | 0.90 |
| | Cetearyl alcohol | 1.00 | 1.03 | 1.02 | 0.99 | 0.95 | 0.93 | 1.04 | 0.90 |

TABLE 16-continued

Creamy foundation

| Component | | Ex. 2 | Ex. 24 | Ex. 25 | Ex. 26 | Ex. 27 | Ex. 28 | Com. EX. 14 | Com. EX. 15 |
|---|---|---|---|---|---|---|---|---|---|
| | Glycerin | — | — | — | — | — | — | — | — |
| | 1,3-Butylene glycol | — | — | — | — | — | — | — | — |
| | Ethylhexyl methoxycinnamate | 3.00 | 3.10 | 3.05 | 2.96 | 2.86 | 2.80 | 3.11 | 2.71 |
| | Sodium hydroxide | — | — | — | — | — | — | — | — |
| | Spheric nylon powder | — | — | — | — | — | — | — | — |
| | Crosslinked type silicone powder | — | — | — | — | — | — | — | — |
| | Magnesium sulfate | — | — | — | — | — | — | — | — |
| | Preservative | trace amount | trace amount | trace amount | trace amount | trace amount | trace amount | trace amount | trace amount |
| Evaluation | Storage stability | G | G | G | G | G | M | B | B |
| | Applicability (ease of spreading) | G | G | G | G | G | M | B | B |
| | Stickiness | G | G | G | G | G | M | B | B |
| | Oily feeling | G | G | G | G | G | G | B | B |
| | Cosmetic-holding ability | G | M | G | G | G | G | B | B |
| | Oily sheen | G | G | M | G | G | G | B | B |

In Examples 24 to 28 and Comparative Examples 14 to 15, the ratio of Component (C) was varied, on the basis of the composition in Example 2. Now, in each Example or Comparative Example, the ratio among the components other than (C) was adjusted to be same as that in Example 2. Within the present invention, good evaluation results were obtained.

The water-in-oil type emulsified cosmetic of the present invention may take various forms such as liquid, solid, cream, paste, gel, mousse, etc., and is useful for make-up cosmetics and sun-care cosmetics such as make-up bases, eye shadows, sunscreens, mascaras, foundations, blushers, eye liners, eyebrow cosmetics, etc.

The invention claimed is:

1. A water-in-oil emulsified cosmetic comprising
   (A) 10 to 60 parts by mass of a diester represented by the following formula (I):

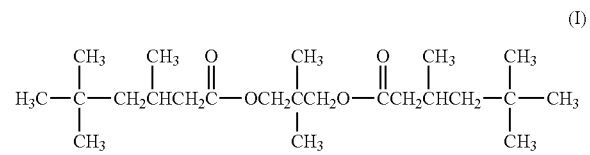

(B) 1.0 to 11 parts by mass of a nonionic surfactant,
   (C) 0.3 to 11 parts by mass of one or more oil soluble thickeners selected from dextrin palmitate and dextrin (palmitate/ethylhexanoate),
   (D) 0.1 to 30 parts by mass of fine particles, and
   (E) 5.0 to 75 parts by mass of water,
   wherein the total of (A), (B), (C), (D) and (E) is 100 parts by mass.

2. The water-in-oil emulsified cosmetic according to claim 1, wherein the amount of the diester represented by the formula (I) is 12 to 55 parts by mass.

3. The water-in-oil emulsified cosmetic according to claim 1, wherein the amount of the diester represented by the formula (I) is 14 to 50 parts by mass.

4. The water-in-oil emulsified cosmetic according to claim 1, wherein the amount of the nonionic surfactant (B) is 1.1 to 9.8 parts by mass.

5. The water-in-oil emulsified cosmetic according to claim 1, wherein the amount of the nonionic surfactant (B) is 1.2 to 9.6 parts by mass.

6. The water-in-oil emulsified cosmetic according to claim 1, wherein the amount of the oil-soluble thickener (C) is 0.4 to 9.8 parts by mass.

7. The water-in-oil emulsified cosmetic according to claim 1, wherein the amount of the oil-soluble thickener (C) is 0.5 to 9.6 parts by mass.

8. The water-in-oil emulsified cosmetic according to claim 1, wherein the amount of the fine particles (D) is 0.2 to 28 parts by mass.

9. The water-in-oil emulsified cosmetic according to claim 1, wherein the amount of the fine particles (D) is 0.3 to 26 parts by mass.

10. The water-in-oil emulsified cosmetic according to claim 1, wherein the amount of water (E) is 10 to 68 parts by mass.

11. The water-in-oil emulsified cosmetic according to claim 1, wherein the amount of water (E) is 15 to 66 parts by mass.

12. The water-in-oil emulsified cosmetic according to claim 1, wherein the nonionic surfactant (B) is at least one selected from the group consisting of sorbitan monoisostearate, lipophilic glycerin monostearate, glyceryl stearate (SE), sorbitan sesquiisostearate, polyglyceryl-2 isostearate, polyglyceryl-2 diisostearate, polyglyceryl-2 triisostearate and sorbitan oleate.

13. The water-in-oil emulsified cosmetic according to claim 1, wherein the nonionic surfactant (B) is at least one selected from the group consisting of sorbitan monoisostearate, lipophilic glycerin monostearate, sorbitan sesquiisostearate, polyglyceryl-2 isostearate and sorbitan oleate.

14. The water-in-oil emulsified cosmetic according to claim 1, wherein the cosmetic is a make-up or sun-care cosmetic.

15. A method of making-up a person comprising applying to the person a cosmetic according to claim 1.

* * * * *